United States Patent [19]

Rubinstein

[11] Patent Number: 5,185,371

[45] Date of Patent: Feb. 9, 1993

[54] METHOD FOR DISINFECTING RED BLOOD CELLS

[75] Inventor: Alan I. Rubinstein, Los Angeles, Calif.

[73] Assignee: University of Southern California, Los Angeles, Calif.

[21] Appl. No.: 492,723

[22] Filed: Mar. 13, 1990

Related U.S. Application Data

[63] Continuation-in-part of Ser. No. 230,839, Aug. 9, 1988, Pat. No. 4,971,760, which is a continuation-in-part of Ser. No. 892,058, Sep. 1, 1986, abandoned, which is a continuation-in-part of Ser. No. 838,253, Mar. 10, 1986, abandoned.

[51] Int. Cl.⁵ ............... A61K 31/05; A61K 31/055; A61K 31/115; A61K 33/18

[52] U.S. Cl. ............................ 422/28; 422/37; 424/605; 424/616; 424/661; 424/666; 424/672; 435/2; 514/694; 514/731; 514/739

[58] Field of Search ............ 422/28, 37; 435/2; 530/412; 424/605, 616, 661, 666, 672; 514/694, 731, 739

[56] References Cited

U.S. PATENT DOCUMENTS

| | | |
|---|---|---|
| Re. 27,359 | 5/1972 | Ilg . |
| Re. 31,779 | 12/1984 | Alliger ........................ 422/28 X |
| 3,031,378 | 4/1962 | Ishidate et al. . |
| 3,100,737 | 8/1963 | Auerswald et al. . |
| 4,314,997 | 2/1982 | Shanbrom . |
| 4,481,189 | 11/1984 | Prince . |
| 4,632,980 | 12/1986 | Zee et al. ........................ 530/380 |
| 4,675,159 | 6/1987 | Al-Sioufi ........................ 422/36 |
| 4,833,165 | 5/1989 | Louderback ..................... 514/694 |

FOREIGN PATENT DOCUMENTS 0112563 7/1984 European Pat. Off. .

OTHER PUBLICATIONS

Inactivation of Lymphadenopathy Associated Virus by Chemical Disinfectants, Spire et al., *The Lancet*, Oct. 20, 1984.

Inactivation of Human T-Cell Lymphotropic Retrovirus (HTLV-III) by LD, Sarin et al., *The New England Journal of Medicine*, Nov. 28, 1985.

*Primary Examiner*—Jill A. Johnston
*Attorney, Agent, or Firm*—Poms, Smith, Lande & Rose

[57] ABSTRACT

A method to inactivate viruses or to disinfect blood products, for instance units of red blood cells, wherein a disinfectant or virus inactivating chemical is made isotonic or nearly isotonic, and wherein the red blood cells are exposed to isotonic disinfectant to inactivate any agent which may be present, for example HIV-1 virus which causes AIDS. The method may also be applied to plasma fractions and corneas.

16 Claims, No Drawings

METHOD FOR DISINFECTING RED BLOOD CELLS

RELATED APPLICATIONS

This is a continuation-in-part of U.S. patent application Ser. No. 230,839, filed Aug. 9, 1988, now U.S. Pat. No. 4,971,760; which in turn was a continuation-in-art of Ser. No. 892,058, filed Sep. 1, 1986, now abandoned; which in turn was a continuation-in-part of Ser. No. 838,253, filed Mar. 10, 1986, now abandoned.

BACKGROUND

1. Field of the Invention

The present invention relates generally to processing human blood products, i.e., whole blood, red blood cells, blood plasma and blood proteins. Additionally, it relates to processing human and animal tissue, e.g., organs and parts of organs used in transplants. More particularly, this invention relates to disinfecting certain blood products and corneas so that they may be used safely and effectively for diagnostic, therapeutic or research purposes.

2. Description of the Related Art

Blood products from human and animal donors are widely used for therapeutic, diagnostic and experimental purposes. Such blood products are subject to contamination by several blood-borne viruses and other micro-organisms. There has been no way to assure that the recipients of blood products or those who handle the products are free from potential exposure to viruses. In particular, the transfusion of human blood products carries a well-known risk of transmitting a number of viruses.

Of particular threat are viruses that appear to cause various forms of hepatitis, including the hepatitis B virus; the non-A, non-B hepatitis virus or viruses. Others of interest are cytomegalovirus and Epstein-Barr virus.

Viruses linked with the incurable and often fatal disease known as acquired immune deficiency syndrome or "AIDS" are probably caused by a retrovirus or group of retroviruses previously denominated "HTLV-III" and other HTLV types—and more currently "HIV," "HIV-1," "HIV-2," "HIV-3" AND "HIV-4." The most common cause of AIDS is thought to be HTLV-III, now usually called HIV-1.

Detection and isolation of such cytopathic retroviruses from patients with AIDS, and certain members of groups that are at high risk for AIDS, have been frequently reported. One such report appears in *Science* 224:500-03 (1984).

Such findings are corroborated by P. S. Savin, et al. in an article entitled "Human T-Lymphotrophic Retroviruses in Adult T-cell Leukemia-Lymphoma and Acquired Immune Deficiency Syndrome," *J. Clinical Immunol.* 4:415-23 (1984). Yet another report is by F. Wong-Staal and R. C. Gallo, "Human T-Lymphotrophic Retroviruses," *Nature* 317:395-402 (1985).

While the hazard of hepatitis and AIDS transmission through transfusion of blood products has received great public attention, the analogous hazard of such transmission through transplantation tissues is a much less familiar matter. Nevertheless, there is a recognized possibility of at least AIDS virus transmission from corneal transplantation, according to *Corneal Surgery Theory, Technique and Tissue*, F. S. Brightbill, ed., p. 53 (Mosby 1986).

Furthermore, contamination of corneas by bacteria and fungi is documented, id. at 52, even though antibacterial solutions are commonly used in pre-transplant storage of corneas—generally within the nutrient medium that supports the corneas.

Disinfecting blood products and tissue products with disinfectants strong enough to significantly inactivate viruses has generally been discounted because they damage cellular blood constituents, and any residual disinfectant in the blood product to be transfused could be hazardous to the recipient of the transfusion.

One disinfectant in use for blood products is beta-propiolactone. In this field, it is usually employed to disinfect plasma preliminary to fractionation. Such a process has been used for isolation of therapeutic immune globulin, Factor VIII and IX, and other blood proteins. Beta-propiolactone, however, is a known carcinogen and hence potentially very dangerous. To the extent that significant residual quantities of this material may remain in the blood product which is actually transfused, the use of propiolactone represents a significant hazard.

U.S. Pat. No. 4,833,165 relates to using as little as 0.1% formaldehyde and/or phenol to inactivate HTLV-III in blood. However, recently available data and information indicate that red blood cells treated with as little as 0.02% formaldehyde and 0.01% phenol are not viable and not suitable for transfusion.

A variety of disinfectants have been used in the medical profession and biomedical industry to disinfect work areas, table tops, walls, surgical instruments, etc., for the purpose of inactivating viruses and micro-organisms associated with blood and tissue products. In particular, U.S. Pat. No. Re. 31,779 relates to the effective use of materials which liberate chlorine dioxide for such purposes. Other compositions which are known in the medical profession to be useful for sterilizing and disinfecting work areas and tools are lower alkyl monohydric alcohols, aldehydes, mineral acids and bases, peroxides, sodium hypochlorite, quaternary ammonium salts and iodine containing compounds. None of these disinfectants have been applied to disinfecting blood products or tissue products. Such compositions in contact with blood and tissue products would cause one to expect resulting damage to the cells and tissue.

Accordingly, there presently is a need to provide a method to disinfect human and animal blood products and human and animal tissue products. In particular, there is a need to disinfect such products so that they can be safely and effectively utilized by a recipient or handled by a user without exposure to harmful viruses and microorganisms.

SUMMARY OF THE DISCLOSURE

It is the object of this invention to provide a composition and method to disinfect blood products and tissue products for their safe and effective use. The invention is based upon the surprising and unexpected discovery that some disinfecting compounds, which heretofore have been discounted as disinfectants for blood products or tissue products, may be used for disinfecting blood products without lysing or otherwise damaging blood cells and tissue cells.

The foregoing object of the present invention is accomplished by combining a particular disinfectant with a diluent in which the disinfectant is soluble and which is isotonic with blood. Surprisingly such a solution will not only disinfect blood products but will do so without damage to the blood product, e.g., blood cells and tissue cells. Such compositions may be used for therapeutic or diagnostic purposes following the disinfectant procedure.

It is presently believed that the disinfectant compositions of the present invention will render blood products, e.g., blood cells, safe, i.e., inactive harmful viruses and virus-like agents present in blood products. As noted, this is accomplished by using certain disinfectants which will not harm the blood products, e.g., cause hemolysis of red blood cells, when dissolved in an aqueous solution which at the proper concentration is isotonic. Disinfectants useful in the present invention are lower alkyl monohydric alcohols (e.g., ethyl and isopropyl alcohol), mineral acids such as hydrochloric acid and sulfuric acid, mineral bases such as alkali metal hydroxides (e.g., sodium and potassium hydroxide) and alkaline earth metal hydroxides (e.g., calcium hydroxide), peroxides which are effective oxidizers, e.g., sodium peroxide, hydrogen peroxide, etc., iodine and iodine complexes which provide iodine when dissolved, e.g., iodine complexes such as providone-iodine; and alkali metal and alkaline earth metal hypochlorites.

Diluents useful in the present invention are aqueous solutions wherein the solute in the proper amount or concentration results in a diluent which is isotonic to the blood or tissue products. Solutes which, when dissolved in water at a proper concentration, are isotonic are known in the art and therefore no detailed description thereof is necessary to the art skilled. Exemplary solutes which are useful in the present invention include sugars such as dextrose, CPD (citrate phosphate dextrose), CPDA-1 (citrate-phosphate-dextrose-adenine), dextran, albumin, alkaline earth metal halides (preferably chlorides) such as calcium chloride, magnesium bromide and calcium fluoride, and alkali metal halide (preferably chlorine) such as sodium chloride potassium bromide.

It is, of course, understood that if red blood cells are to be disinfected, the disinfectant composition must be isotonic to red blood cells. For example, when the disinfectant is an alcohol, e.g., ethanol, the ethanol itself exerts an osmotic gradient. Thus, a relatively high concentration of ethanol, e.g., 20% to 35%, will be diluted in a diluent which is slightly hypotonic with respect to red blood cells. Once the diluent aqueous solution is added to the alcohol, at a certain concentration of alcohol the solution of disinfectant (ethanol) and diluent will be isotonic with respect to the red blood cells. For small concentrations of disinfectant, the diluent solution will itself be isotonic, e.g., 0.9% saline or normal saline. Thus, a disinfectant composition consisting of a substantially isotonic solution of 10 mM NaOH will be 10 mM NaOH in 0.9% saline.

This invention may be practiced using economical procedures which are easily adapted to existing handling techniques for blood products and tissue products. For blood products, this invention can be implemented even while the blood product is in a collection bag. For corneas (or parts thereof), the method can be implemented with only minor, non-disruptive departure from familiar surgical protocols.

In general, the method of this invention consists of washing the cellular blood constituent, plasma or platelets, or tissue in an isotonic solution of disinfectant. An important limitation in choosing the disinfectant and the isotonic medium is that they must be compatible and non-reactive.

The disinfectant concentration and the time required to effectively inactivate any harmful substance is dependent upon the disinfectant strength, suitable concentrations and disinfecting times will become evident in the more detailed description of the invention and the exemplary embodiments.

After washing the cellular blood constituent, plasma or platelets, or tissue, the disinfectant is separated from the disinfecting composition. The separation is accomplished by washing the disinfected composition in a medium which is isotonic solution with blood until the disinfectant is ireduced to a safe or insignificant level. Preferably the medium is the same as that used to disinfect the blood or tissue product.

DETAILED DESCRIPTION OF THE INVENTION

The present invention involves the effective and safe disinfection of blood products and tissue products. The invention has wide application to all blood products such as whole blood for transfusion, blood cells, blood plasma and blood proteins. It is also suitable for disinfecting tissue products intended for transplant from a donor to a recipient.

In accordance with the preferred method for disinfecting blood products, a method is provided in which any virus in the whole blood and blood products is inactivated. Additionally, the blood products may be used subsequently for therapeutic or diagnostic purposes in a safe and effective manner. The invention is based upon the unexpected discovery that isotonic compositions which contain many disinfectants do not lyse blood cells or cause harm to blood products.

In accordance with the present invention, blood products are mixed with a disinfectant composition which is substantially isotonic with blood. The disinfectant may be any of a number of known disinfectants or substances which inactivate viruses. Included in this group are lower alkyl monohydric alcohols, mineral acids and mineral bases, peroxides, Lysol, (alkyl and chloro substituted phenols), iodine complexes and hypochlorites.

In accordance with this invention, isotonic solutions which may be used as diluents for the disinfectant are normal saline solution or 0.9% aqueous sodium chloride, 5% aqueous dextrose, suitable dextran solutions, sugar solutions and albumin solutions, as well as solutions of alkali earth metal salts. Solution containing additives such as CPD (citrate phosphate dextrose) and CPDA-1 are also suitable. The disinfectant concentration and disinfecting times are dependent upon the nature of the disinfectant which is used in the procedure. Appropriate concentrations and times as well as suitable isotonic diluents will become apparent upon consideration of the detailed examples which follow.

After the disinfectant and blood product are mixed sufficiently to inactivate any viruses that may be present, the disinfectant is separated from the blood products. The separation preferentially involves washing the blood products in an automated cell washer or semi-automated cell washer with an isotonic solution until the disinfectant is substantially removed.

In a case where the blood proteins are of interest, the disinfectant separation step advantageously includes precipitating out the plasma proteins in a generally conventional fashion. Preferably this precipitation is produced by contact with ammonium sulfate or like precipitating agent, generally at a concentration of 80% or less.

The proteins are then resuspended in a relatively small volume of isotonic solution, preferably normal saline, and exhaustively dialysed against a relatively large volume of normal saline. The dialysis substep effectively reduces the concentration of disinfectant as well as precipitating agent to a negligible level. If desired, the dialysis substep may be replaced by high speed centrifugation using conventional techniques for separating the proteins.

When practicing the present invention for disinfecting tissue products, the same general techniques which apply for blood product are applicable. A particularly suitable tissue product is corneas used for transplant purposes. A disinfectant composition is prepared in a solution which is isotonic with blood. The tissue product is exposed to the disinfecting composition until any viruses or micro-organisms present are inactivated. The disinfectant is then separated from the tissue by immersing and rinsing the tissue in an isotonic solution until no detectable concentration of disinfectant remains with the tissue.

In practicing the present invention and in choosing a disinfectant which itself exerts an osmotic gradient, the diluent must be slightly hypotonic with respect to red blood cells. This is particularly applicable when the disinfectant is used in relatively high concentrations. Accordingly, when ethanol is the disinfectant and it is used at concentrations from about 20% to about 35%, the diluent must be slightly hypotonic. Thus, if the diluent is a saline solution, it will be less than 0.9%.

It is also within the scope of the present invention to combine isotonic diluents. This is particularly applicable when disinfecting red blood cells because commercial collective units of red blood cells are frequently stored in anti-coagulant components which are isotonic, e.g., ACD (acid, citrate, dextrose), CPD (citrate, phosphate, dextrose), CPD-A (CPD and adenine). When sterilizing collective units of red blood cells stored in the above mentioned anti-coagulant isotonic solutions, the disinfectant composition may be prepared in a different isotonic diluent, e.g., normal saline, and combined with the anti-coagulant solution.

The method of this invention may be practiced by assembling the various chemical ingredients in any of a great number of sequences. Thus, for example, sodium chloride may be premixed with disinfectant for commercial packaging, and this pre-mixture then diluted with distilled, sterile water at the point of use.

The primary controlling considerations in these various possible sequences is that upon addition of diluent water, the resulting mixture is substantially isotonic with blood and the isotonic medium must be unreactive and compatible with the disinfectant. Aside from considerations of commercial practicality, the particular sequence employed is, by and large, immaterial to the practice of this invention.

Suitable disinfecting times will become apparent when considering the detailed examples which follow. It is understood that the disinfection time may be adjusted in accordance with well-known principles of chemistry to accommodate treatment of the tissue while it is refrigerated, or even while it is heated. Again, care must be taken in using such lower or higher temperatures to avoid damage to the tissue from the temperature exposure itself—or from the combination of conditions of temperature and disinfecting substance.

Practicing this invention procedure is practical, useful, streamlined and economical. Its advantages particularly include eliminating transmission of viruses and micro-organisms in blood transfusions and tissue transplants.

In particular, it is verified that the disinfecting process leaves substantially intact certain substances that are present in blood and are recognized as indicators of normal or healthy blood constituent activity. These verifications will be described in a later section of this document. In short, the method of the present invention disinfects blood constituents without damaging them.

All of the foregoing operational principles and advantages of the present invention will be more fully appreciated upon consideration of the following detailed examples.

EXAMPLE 1

Sterilization Technique

Certain constituents of human blood are disinfected as follows. First, if desired, the cellular blood constituents may be separated from the plasma and from plasma fractions or proteins such as coagulating factors, globulins and so forth.

If this is not done, however, there is no effect on the particular constituents of interest. Moreover, with the refinements of the invention described herein, it is possible to preserve the other fractions (with or without disinfecting them) through the disinfection process.

Next, the blood product containing the constituents of interest is exposed for a suitable time to a disinfectant solution. The solution may be prepared in any of a great range of concentrations and in a variety of ways. The disinfectant solution is isotonic with respect to red blood cells.

In standard procedure for collection and storage of red blood cells, the cells are first separated from whole blood by centrifugation and then may be washed in normal saline solution. Since in such a procedure the cells may be in saline already, one convenient way of practicing my invention for red blood cells may be to simply add the disinfectant solution in a relatively concentrated from to the mixture of red cells and saline as washing begins, or after washing is complete but before the saline is removed.

Such addition should be performed gradually, and while the red cells and saline solution are mixed. These precautions should be adequate to minimize exposure of any small portion of the cells to a large quantity of the disinfectant, and to ensure adequate uniform exposure of all cells to disinfectant.

Another possibility for red blood cells is to follow the usual washing procedure, except for the substitution of the disinfectant and saline solution for saline alone. In either event, the disinfectant can be performed either while the cells are in their original collection bag suspended in CPD or CPDA-1 or other anticoagulant, or in a larger bag or other container; or in a red blood cell bag containing ADSOL ® or other RBC preservative solution such as AS-1.

It is desirable to use a larger bag, so that the volume of disinfectant is less than half that of the bag, and the total volume of disinfectant and cells is substantially less than the total volume of the bag. My point here is simply to allow ample excess volume for thorough and effective mixing, so that none of the cells is overexposed and all are adequately exposed to the disinfectant.

Platelets, by contrast, are not usually washed in the present standard procedures for blood treatment. For present purposes, however, they are advantageously washed using any of the procedures described above for red blood cells.

Procedures for treatment and segregation of plasma proteins have been set forth above. General procedures for treatment of corneal and scleral tissue have also been outlined but, as will be understood, the disinfection arrangements must be accommodated to the special needs and circumstances of the harvesting, nutrive and surgical environment.

Following exposure of the blood product to the disinfectant, the disinfectant is removed from the subject constituent. Such removal advantageously includes washing, with or without the aid of automation. An automated cell washer (such as a COBE cell washer) may be used to particular advantage for red blood cells or for platelets.

The washer may be programmed to mix the disinfectant with the constituent for a few seconds, or for a few minutes. The washer may also be programmed to then wash the constituent automatically.

Automation increases the utility of the invention, since through the use of automation red blood cells, platelets, and even plasma proteins, may be washed rapidly and the invention practiced on a production scale. Disinfectant composition, as well as disinfection times, may be varied without departing from the scope and spirit of the invention.

EXAMPLE 2

To verify more fully that red blood cells treated with disinfectant were still viable and thus suitable for transfusion, assays were performed to determine the oxygen transfer capability and enzymatic activity of two representative constituents of the disinfected red blood cells.

The ATP and 2,3-DPG of the disinfected red blood cells were compared with those of the untreated cells. These two enzymes are considered important predictors of the viability and suitability for transfusion of red blood cells. Results are displayed in Table I.

TABLE I

| Set A | RBC ATP μmoles/gmHb | RBC 2,3-DPG μmoles/gmHb |
|---|---|---|
| 1. Control (untreated RBC's) | 3.03 | 11.7 |
| 2. RBC's treated with 10% ethyl alcohol in saline for 5 minutes | 2.53 | 12.4 |
| 3. RBC's treated with 30 mM NaOH in normal saline for 5 minutes | 1.29 | 10.7 |
| 4. RBC's treated with 0.02% formaldehyde in normal saline for 5 minutes | 0.89 | 11.8 |
| 5. RBC's treated with 20% ethyl alcohol in saline for 5 minutes | 1.70 | 12.6 |

| Set B | RBC ATP Zero Time | RBC ATP After Two Hours Incubation |
|---|---|---|
| 1. Control (Untreated RBC's) | 3.41 | 3.73 |
| 2. RBC's treated with 10% ethyl alcohol in normal saline for 2-5 minutes | 2.61 | 3.33 |
| 3. RBC's treated with 10 mM NaOH in normal saline for 2-5 minutes | 1.57 | 2.43 |
| 4. RBC's treated with (0.02%) formaldehyde in normal saline for 2-5 minutes | 1.0 | 0.42 |
| 5. RBC's treated with 20% ethyl alcohol in normal saline for 2-5 minutes | 2.22 | 3.30 |

| Sample | ATP μmoles/gmHb | | 2,3 DPG μmoles/gmHb | |
|---|---|---|---|---|
| | 0 time | 2 hrs. | 0 time | 2 hrs. |
| Set C | | | | |
| RBC's treated with 50 mM HCl in normal saline for 2-5 minutes | 4.09 | 3.44 | 9.9 | 9.0 |
| RBC's treated with 0.3% hydrogen peroxide in normal saline for 2-5 minutes | 4.35 | 4.12 | 10.7 | 10.2 |
| RBC's treated with 0.5% Lysol in normal saline for 2-5 minutes | 4.63 | 4.39 | 12.9 | 10.9 |
| RBC's treated with 0.1% sodium hypochlorite in normal saline for 2-5 minutes | 3.54 | 3.46 | 9.76 | 9.76 |
| RBC's control in normal saline | 3.80 | 3.66 | 9.93 | 9.93 |
| Set D | | | | |
| Control RBC's in normal saline | 3.87 | 3.09 | 0.5 | 0.5 |
| RBC's treated with 5% isopropyl alcohol in 0.45% saline | 3.31 | 2.96 | 0.7 | 1.0 |
| RBC's treated with 0.05% providone-lodine in normal saline | 2.28 | 2.65 | 2.6 | 3.0 |

In viewing the results for each set of samples, it is important to evaluate the data with respect to the values obtained for the red blood cell (RBC) controls for that set. While it is preferable to have an ATP activity above 3.6 micromoles/Gm Hb and a 2,3 DPG activity above 12 micromoles/Gm Hb for transfusion purposes, the RBCs used in these studies were handled extensively prior to the initiation of the experiments. Excess handling will cause some RBC damage. Therefore, values less than 3.6 micromoles/Gm Hb for ATP and less than 12 micromoles/Gm Hb for 2,3 DPG indicate non-functional RBCs only when the controls for that set have high ATP and 2,3 DPG activity.

A second indicator of viable RBCs is the ability of the RBC to regenerate as indicated by an increase in ATP concentration. Disinfected RBCs which show an increase in ATP activity after a two hour incubation period in nutrients are considered viable since they have the potential of increasing their enzyme function. This indicator again is significant only when the control RBCs also show regeneration capabilities. When the control RBC drop in activity, there is an indication of irreversible damage due to handling for that set of red blood cells.

As detailed in the examples given in Table I, sets A and B, there was no evidence of loss of red blood cell viability following disinfection of red blood cells exposed to 10% ethanol in 5% dextrose in water, 20% ethanol in normal saline, or 10 mM NaOH in normal saline. The low ATP values observed in Set A are saved by the ability of the cells to regenerate as indicated in Set B. Of the disinfectants tested in Set A and Set B, 0.02% formaldehyde in normal saline was not effective and therefore not a suitable disinfectant.

The examples in Table I, Set C, indicate that RBCs treated with 50 mM HCl, 0.3% hydrogen peroxide, 0.5% Lysol, and 0.1% sodium hypochlorite in normal saline retain their viability. Set D shows that disinfectants of isopropyl alcohol and providone-iodine are also effective for use with red blood cells. Although the activities for these are low and regenerative capabilities are not indicated, the control cells show comparable results.

It is clear that different disinfectants may be diluted with solutions to give disinfectants which are isotonic with respect to blood and will not harm or significantly affect RBC's. Thus, units of RBC's may be effectively disinfected and then may be transfused safely.

Some useful final disinfectant concentrations and disinfection times are: 0.001% to 1% sodium hypochlorite for 15 seconds to 5 minutes; 0.005% to 0.5% glutaraldehyde for 1 minute to 5 minutes; 10 mM to 100 mM sodium hydroxide for 30 seconds to 5 minutes; 1% to 25% ethanol for 30 seconds to 5 minutes; 0.05% to 0.5% hydrogen peroxide for 30 seconds to 5 minutes; 1% to 30% isopropyl alcohol for 1 minute–5 minutes; 0.005% to 1% Lysol for 30 seconds to five minutes; detergents (e.g., Nonidet p-40) at a concentration of 0.01% to 1% for 15 seconds to 5 minutes and providone-iodine solutions at dilutions of 0.01% to 0.5% for 10one or seconds to 5 minutes.

The length of time for disinfection is related to the concentration of disinfectant. Thus, a very weak concentration of disinfectant may take several minutes to significantly disinfect; however, such long disinfection times are not practical and thus, this invention prefers disinfection times from 30 seconds to five minutes. This is most practical to use for a large blood bank facility.

I therefore conclude that red blood cells are safe and suitable for human transfusion, following treatment as described herein. These red blood cells carry a much lower risk or total absence of risk of transmitting the harmful substances enumerated earlier, and others.

EXAMPLE 3

Red Blood Cell Survival Studies

Method followed:
(1) Sixty ml of fresh peripheral blood were drawn into a heparinized syringe.
(2) Cells were separated from plasma (2,000 rpm for 8 minutes on Beckman TJ-6 centrifuge).
(3) Separated cells were divided into four aliquots of four ml each:
   To one aliquot 4 ml of normal (0.9%) saline was added.
   To the second, four ml of a 30 mM solution of NaOH in normal saline was added.
   To the third, four ml of 20% by volume of ethyl alcohol in normal saline was added.
(4) All samples were incubated at room temperature for five minutes.
(5) Samples were then centrifuged (2,000 rpm for eight minutes on Beckman TJ-6).

Results: In all cases, supernatants were equally clear and free of visible free hemoglobin as the control sample. In all cases, the RBC separated after centrifugation. There was no evidence of hemolysis.

Wright stains performed on RBC from each of the four samples showed normal RBC morphology. White cells were also seen and were normal in appearance.

Interpretation: Treatment of RBC's with either 30 mM NaOH or 20% ethyl alcohol in isotonic solution causes no RBC hemolysis.

EXAMPLE 4

RBC survival studies after treatment with sterilants:
Method followed:
(1) Fifty ml of fresh blood from healthy donors were drawn into heparinized tubes.
(2) Cells were separated from plasma (Beckman TJ-6 centrifuge).
(3) Four ml of cells mixed with equal volumes of one of each of either
   Sample 1: normal saline (0.9%)
   Sample 2: isopropyl alcohol 5% in ½ normal saline (0.45%)
   Sample 3: Providone-iodine 0.5% in 0.9% saline
(4) Cells and sterilants were incubated at room temperature for two minutes.
(5) Control cells (Sample 1) were incubated at room temperature for two minutes.
(6) Samples were centrifuged (Beckman TJ-6 centrifuge)
(7) Samples were washed in five ml normal saline, followed by another centrifugation as before.

Results: There was no hemolysis seen in any of the three samples; supernatants removed (step 6) from all three preparations were equally free of hemoglobin.

Microscopic examination of cells on Wright stain showed normal red cell morphology.

Conclusion: No evidence of hemolysis or red cell damage following treatment with the sterilant solutions.

EXAMPLE 5

Method followed:
(1) Sixty ml of fresh blood from healthy donors were drawn into heparinized tubes.
(2) Cells were separated from plasma (2,000 rpm on Beckman TJ-6 centrifuge).
(3) Four ml of cells mixed with equal volumes of one of each of the following solutions:
   Sample 1: normal saline (0.9% NaCl) (control)
   Sample 2: 0.3% hydrogen peroxide
   Sample 3: 0.5% Lysol brand disinfectant (active ingredients: o-phenylphenol o-benzyl-o-chlorophenol, soap, ethyl alcohol, xylenol, isopropyl alcohol, tetrasodium ethylenediamine tetraacetate)
   Sample 4: 0.1% Clorox brand bleach (active ingredient sodium hypochlorite)
   Sample 5: hydrochloric acid (HCl) 0.05 Molar.

Dilutions of all sterilants to the percentages mentioned above were made in normal saline.
(4) Cells and sterilant were incubated at room temperature for two minutes, as were the control cells (Sample 1)
(5) All samples were centrifuged (2,000 rpm on Beckman TJ-6)
(6) Samples were washed in five ml normal saline
(7) Samples were centrifuged again as before.

Results: No hemolysis was seen in Samples 1 through 5; supernatants of all five were clear and free of free hemoglobin.

Microscopic examination of cells from Samples 1 through 5 showed normal red cell morphology.

Conclusion: There was no evidence of hemolysis following treatment with the sterilants; red blood cells were unaffected by the exposure.

EXAMPLE 6

RBC survival studies following treatment with sterilant solutions:

Method:
(1) Sixty ml of fresh blood were drawn from healthy donors and collected in heparinized tubes.
(2) Cells were separated from plasma (Beckman TJ-6 centrifuge).
(3) Three ml of cells added to an equal volume to one of each of either
  Sample 1: Hydrochloric acid (HCl) 1 mM in normal saline (0.9% NaCl)
  Sample 2: phenol 0.001% in 0.9% NaCl
  Sample 3: Betadine solution (providone iodine) 0.1%, in 0.9% NaCl
  Sample 4: Quaternary ammonium chloride compounds, Benzyl-$C_{12}$-18-Alkyl Dimethyl Ammonium chloride 0.00005% (benzalkonium chloride) diluted in 0.9% NaCl.
  Sample 5: 0.9 NaCl (control)
(4) Cells and sterilants (or control) were incubated at room temperature (25° C.) for two minutes.
(5) Samples centrifuged (Beckman TJ-6 centrifuge); sterilant removed.
(6) Samples washed in five ml normal saline (0.9% NaCl), followed by another centrifugation as previously described.
(7) Normal saline was removed. Samples washed an additional four times with normal saline.

Results: No hemolysis seen in supernatants of either Samples 1 through 4 or in the control (Sample 5) following incubation (Step 4); no free hemoglobin was seen. Microscopic examination of cells on Wright stain showed normal red cell morphology.

Conclusion: No evidence of hemolysis or red cell damage following treatment with the sterilant solutions used in Samples 1 through 4.

EXAMPLE 7

RBC Survival Studies Following Treatment with Sterilant Solutions

Method followed:
1. Sixty ml of fresh blood were drawn from healthy donors and collected in heparinized tubes.
2. Cells were separated from plasma (Beckman TJ-6 centrifuge).
3. Three ml of cells mixed with equal volumes of one of the following solutions. Sterilants are expressed as percent (%) volume made up in normal saline except as noted.
  Sample 1: normal saline (0.9%) NaCl) (control sample)
  Sample 2: phenol 0.08%
  Sample 3: formaldehyde 0.08%
  Sample 4: EtOH 10% in Dextrose 5% in water (D5W).
4. Cells and sterilants (or control) incubated at room temperature for five minutes.
5. Samples centrifuged to pellet cells (Beckman TJ-6 centrifuge).
6. Five ml of normal saline added to each sample to wash remaining sterilant.
7. Cells centrifuged down.
8. Normal saline wash repeated additional four times.

Results: No hemolysis seen in Samples 1 and 4; supernatant removed following incubation (step 4) were free of visual free hemoglobin.

Sample 2 (phenol 0.08%) showed substantial hemolysis; the supernatant removed at step 4 was markedly discolored with free hemoglobin.

Sample 3 (formaldehyde 0.08%) showed hemolysis; the supernatant removed at step 4 showed a visible amount of discoloration with free hemoglobin.

Conclusion: Incubation with EtOH in D5W causes no RBC hemolysis. Cells are intact. Treatment with 0.08% phenol and 0.08% formaldehyde induces substantial RBC hemolysis.

EXAMPLE 8

Infectivity Testing of HIV in RBC Samples After Treatment With Candidate Sterilizing Agents Procedure:
1. Add HIV-1 virus stock (IIIB strain) to RBC solution. Mix $10^6$ $TCID_{50}$/ml stock with cells for final 1/100 solution. 100 ul of virus plus 0.9 ml of RBC mixture.
2. Add an equal volume of sterilizing agent, or control solution, to virus+RBC mixture.
3. Prepare serial dilutions of treated virus+RBC+agent mixture in 96-well plates. Start with 200 ul in first well, serially dilute half by transferring 100 ul to wells containing 100 ul of medium for 11 columns. Perform in quadruplicate.
4. Add 100 ul of C8166 indicator cells ($2 \times 10^6$/ml) per well.
5. Incubate at 37°, 5% $CO_2$ for four days.
6. Split wells ¼ into fresh plates.
7. At day seven read plates microscopically for general morphology and syncytia. The presence of syncytia indicates HIV infection.

Results: Each row begins with 100 ul of 1/100 dilution of virus inoculum, then is serially diluted by one-half increments for a total of 12 wells. The viral titer is defined as the lowest dilution of the inoculum producing evidence of infection in two or more of the quadruplicate wells.

Wells 1 and 2 (viral dilutions 1/100, 1/200), for all samples, contained too many RBC to observe the morphology of the indicator C8166 cells. Wells 3, 4, 5 (viral dilutions 1/400 to 1/1600) contained a mixture of RBC and C8166 cells but, for most samples, the C8166 cells maintained apparently normal morphology and proliferation.

| Sterilants | Viral Titer | Comments |
| --- | --- | --- |
| 1. Ethyl Alcohol 20% in normal saline | <1/200 | No syncytia observed |
| 2. NaOH 30 mM in normal saline | <1/200 | No syncytia observed |
| 3. Sodium hypochlorite 0.1% in normal saline | <1/200 | No syncytia observed |
| 4. HCl 0.05 M in normal saline | <1/200 | No syncytia observed |
| 5. Normal saline control | 1/6400 | No viable C8166 cells observed at viral dilutions 1/400 to 1/1600. In 3 of 4 wells at 1/3200 viral dilution, all C8166 cells were dead, but 1 of 4 showed syncytia. At 1/6400 viral dilution 3 of 4 wells |

-continued

| Sterilants | Viral Titer | Comments |
|---|---|---|
| | | showed dramatic syncytia |
| 6. Formaldehyde 0.02% in normal saline | 1/200 | No syncytia observed |

Results: All the tested sterilants reduced the viral titer by a factor of 1/320 or more. Thus, it has been shown that several sterilants diluted in normal saline (isotonic) were able to inactivate HIV-1.

It will be understood that the foregoing disclosure is intended to be merely exemplary, and not to limit the scope of the invention—which is to be determined by reference to the appended claims.

I claim:

1. A method for treating red blood cells to inactivate HIV viruses contained therein, said method comprising the steps of:
    mixing the red blood cells with a disinfectant composition for a sufficient time to inactivate said HIV viruses, said disinfectant composition comprising at least one disinfectant in an amount sufficiently high to inactivate said viruses and sufficiently low to avoid hemolysis, and said disinfectant selected from the group consisting of ethyl alcohol, isopropyl alcohol, sodium hydroxide, hydrochloric acid, formaldehyde, povidone-iodine, hydrogen peroxide, a combination of o-phenylphenol, o-benzyl-o-cholorophenol, ethyl alcohol, xylenol, isopropyl alcohol, and tetrasodium ethylenediamine tetraacetate, and sodium hypochlorite, and a diluent, said diluent consisting essentially of water and a solute which, when the solute is at the proper concentration, the disinfectant composition is substantially isotonic with blood; and
    separating the disinfectant from the red blood cells, said red blood cells being substantially viable for diagnostic or therapeutic use.

2. The claim according to claim 1 wherein the disinfectant composition further contains one or more additives selected from the group consisting of phosphates, adenine, inosine, citrate and phenylpyruvic.

3. The method according to claim 2 wherein separating the disinfectant consists of washing the red blood cells and disinfectant with a solution substantially isotonic with blood until the disinfectant is substantially removed.

4. The method according to claim 1 wherein mixing the red blood cells and disinfectant composition and separating the disinfectant is performed with an automatic or semi-automatic cell washer.

5. The method of claim 1 wherein said disinfectant is ethyl alcohol and said amount is from about 1% to about 25%.

6. The method according to claim 5 wherein the disinfecting time is from about 30 seconds to 5 minutes.

7. The method of claim 1 wherein said disinfectant is hydrochloric acid and said amount is an HCl concentration of from about 10 mM to about 50 mM.

8. The method of claim 1 wherein said disinfectant is sodium hydroxide and said amount is a sodium hydroxide concentration of from about 10 mM to about 100 mM.

9. The method of claim 1 wherein said disinfectant is povidone-iodine and said amount is from about 0.01% to about 0.5%.

10. The method according to claim 9 wherein said disinfecting time is from about 10 seconds to 5 minutes.

11. The method of claim 1 wherein said disinfectant is hydrogen peroxide and said amount is from about 0.01% to about 0.5%.

12. The method according to claim 11 wherein the disinfecting time is from about 30 seconds to about 5 minutes.

13. The method of claim 1 wherein said disinfectant is isopropyl alcohol and said amount is from about 5% to 30%.

14. The method of claim 1 wherein said diluent is an aqueous solution of one or more solute selected from the group consisting of sodium chloride, dextrose, citrate-phosphate-dextrose, glucose, citrate-phosphate-dextrose-adenine, salts of alkali earth metals, dextrans, albumin, saline-mannitol-dextrose-adenine.

15. A disinfectant composition for inactivating HIV viruses in red blood cells, said composition consisting essentially of:
    a solution of a diluent consisting essentially of an isotonic solute, said isotonic solute present in amount sufficient to cause said disinfectant composition to be substantially isotonic with blood; and
    a disinfectant in an amount sufficiently high to inactivate HIV viruses and sufficiently low to avoid hemolysis, said disinfectant selected from the group consisting of ethyl alcohol, isopropyl alcohol, sodium hydroxide, hydrochloric acid, formaldehyde, povidone-iodine, hydrogen peroxide, a combination of o-phenylphenol, o-benzyl-o-chlorophenol, ethyl alcohol, xylenol, isopropyl alcohol, and tetrasodium ethylenediamine tetraacetate and sodium hypochlorite.

16. The composition of claim 15 wherein said dilutent solution is an aqueous solution of isotonic solutes, said solutes selected from the group consisting of sodium chloride, dextrose, citrate-phosphate-dextrose, glucose, citrate-phosphate-dextrose-adenine, salts of alkali earth metals, dextrans, albumin, saline-mannitol-dextrose-adenine.

* * * * *